(12) United States Patent
Kameshima

(10) Patent No.: US 7,247,758 B2
(45) Date of Patent: Jul. 24, 2007

(54) METHOD FOR PRODUCING 2,3,6,7,10,11-HEXAHYDROXYTRIPHENYLENE

(75) Inventor: Takashi Kameshima, Tokushima (JP)

(73) Assignee: Otsuka Chemical Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 10/576,738

(22) PCT Filed: Oct. 20, 2004

(86) PCT No.: PCT/JP2004/015865

§ 371 (c)(1),
(2), (4) Date: Apr. 21, 2006

(87) PCT Pub. No.: WO2005/037754

PCT Pub. Date: Apr. 28, 2005

(65) Prior Publication Data

US 2007/0093682 A1 Apr. 26, 2007

(30) Foreign Application Priority Data

Oct. 22, 2003 (JP) .............................. 2003-361500

(51) Int. Cl.
*C07C 33/26* (2006.01)
*C07C 33/28* (2006.01)
(52) U.S. Cl. ...................................................... 568/811
(58) Field of Classification Search ..................... None
See application file for complete search history.

(56) References Cited

FOREIGN PATENT DOCUMENTS

| JP | 9-502164 A | | 3/1997 |
|----|------------|---|--------|
| JP | 9-118642 A | | 5/1997 |
| JP | 11-255690 | * | 9/1999 |
| JP | 2003-201263 A | | 7/2003 |

* cited by examiner

*Primary Examiner*—Thurman K. Page
*Assistant Examiner*—Kellette Gale
(74) *Attorney, Agent, or Firm*—Fitch Even Tabin & Flannery

(57) ABSTRACT

The present invention provides a simple and efficient method for producing high-purity 2,3,6,7,10,11-hexahydroxytriphenylene on an industrial scale. The method for producing 2,3,6,7,10,11-hexahydroxytriphenylene comprises reacting catechol with peroxide.

10 Claims, No Drawings

METHOD FOR PRODUCING 2,3,6,7,10,11-HEXAHYDROXYTRIPHENYLENE

This Application is the National Phase of International Application No. PCT/2004/015865 filed Oct. 20, 2004, which designated the U.S. and was not published under PCT Article 21(2) in English, and this application claims, via the aforesaid International Application, the foreign priority benefit of and claims the priority from Japanese Application No. 2003-361500, filed Oct. 22, 2003, the complete disclosures of which are incorporated herein by reference.

TECHNICAL FIELD

The present invention relates to a method for producing 2,3,6,7,10,11-hexahydroxytriphenylene.

BACKGROUND ART 2,3,6,7,10,11-hexahydroxytriphenylene (hereinafter also referred to as "HHTP") is a compound useful as a starting material for the preparation of functional organic materials such as discotic liquid crystals.

Conventionally, HHTP has been manufactured by, for example, a method which involves trimerization of catechol using a transition metal compound (such as ferric chrolide) to give HHTP-transition metal complex(es) and/or quinone form(s) of HHTP which are subjected to a reduction process (see, for example, Japanese Unexamined Patent Publication No. 1993/118642).

With this method, however, it is not easy to produce HHTP with high purity, and therefore too many purification steps are required. Further, HHTP produced by this method suffers from a serious problem in that it does not exhibit desired properties as a functional organic material because of its blackened appearance. Another problem with this method is that because it uses large quantities of dangerous and environmentally hazardous transition metal compounds such as ferric chloride, a great deal of industrial effort and resources are needed for post-reaction treatment.

DISCLOSURE OF THE INVENTION

As described above, the conventional method for producing HHTP from catechol and a metal oxidizing agent suffers from problems such as the difficulty in producing high-purity HHTP. The present invention aims to provide a simple and efficient method of producing high-purity HHTP on an industrial scale as a solution to the above-described problems.

In order to overcome the above-described problems, the present inventors conducted research into a variety of oxidizing agents for enabling oxidative trimerization of catechol. As a result, the inventors found that high-purity HHTP can be manufactured in a simple and efficient manner using a peroxide. On the basis of this finding, the inventors continued further research to accomplish the present invention.

The invention relates to methods of producing HHTP summarized below:

Item 1. A method for producing 2,3,6,7,10,11-hexahydroxytriphenylene comprising reacting catechol with a peroxide.

Item 2. A method according to Item 1, wherein the peroxide is a persulfate.

Item 3. A method according to Item 1, wherein the peroxide is at least one member selected from the group consisting of sodium persulfate, potassium persulfate and ammonium persulfate.

Item 4. A method according to Item 1, wherein the peroxide is ammonium persulfate.

Item 5. A method according to Item 1, wherein the peroxide is hydrogen peroxide.

Item 6. A method according to Item 1, wherein the peroxide is used in a proportion of from 0.5 to 10 moles per mole of catechol.

Item 7. A method according to Item 2, wherein the persulfate is used in a proportion of from 0.5 to 10 moles per mole of catechol.

Item 8. A method according to any one of Items 1 to 7, wherein the reaction is carried out in the presence of acid.

Item 9. A method according to Item 8, wherein the acid used is sulfuric acid or perchloric acid.

Item 10. A method according to Item 8, wherein the acid used is a 50 to 80 wt % aqueous solution of sulfuric acid or a 50 to 80 wt % aqueous solution of perchloric acid.

Further, the present invention encompasses the following aspects:

Item 11. A method according to Item 1, wherein the peroxide is a 30 to 65 wt % aqueous solution of hydrogen peroxide.

Item 12. A method according to Item 1, further comprising treating the reaction product of catechol and the peroxide with an adsorbent or adsorbents.

Item 13. A method according to Item 1, further comprising treating the reaction product of catechol and the peroxide with an adsorbent or adsorbents, and separating 2,3,6,7,10,11-hexahydroxytriphenylene using a solvent including water and acetone.

Item 14. A method according to any one of Items 1 to 13, wherein a solvate of 2,3,6,7,10,11-hexahydroxytriphenylene is produced.

DETAILED DESCRIPTION OF THE INVENTION

The present invention is described in detail below.

The invention relates to a method for producing 2,3,6,7,10,11-hexahydroxytriphenylene wherein catechol is reacted with a peroxide.

Examples of peroxides include persulfates, hydrogen peroxide, etc.

Examples of persulfates include sodium persulfate, potassium persulfate, ammonium persulfate, etc. Of these, ammonium persulfate is particularly preferable. Persulfate is usually used in a proportion of from 0.5 to 10 moles, preferably from 0.8 to 3 moles, and more preferably from 0.9 to 2 moles, per mole of catechol.

Useful examples of hydrogen peroxide include high-purity hydrogen peroxide, aqueous solutions of hydrogen peroxide, ethereal solutions of hydrogen peroxide, etc. Considering safety of handling and industrial availability, a 30 to 65 wt % aqueous solution of hydrogen peroxide is preferable, and a 30 to 60 wt % aqueous solution of hydrogen peroxide is particularly preferable. Hydrogen peroxide is usually used in a proportion of from 0.5 to 10 moles, preferably from 0.8 to 3 moles, and more preferably from 0.9 to 2 moles, per mole of catechol.

Of these peroxides, persulfate is preferable to hydrogen peroxide in terms of HHTP yields.

A solvent is preferably used in carrying out the reaction according to the invention. Examples of solvents include water; alcohol solvents such as methanol, ethanol, n-propanol, isopropanol, and the like; ketone solvents such as acetone, methyl ethyl ketone, and the like; ethereal solvents such as THF, 1,4-dioxane, and the like; halogen-containing solvents such as dichloromethane, trichloromethane, and the like; aromatic hydrocarbon solvents such as toluene, xylene, and the like; ester solvents such as ethyl acetate, methyl acetate, and the like; and aprotic organic polar solvents such as DMF, DMSO, and the like. Such solvents can be used singly or in combination. Among these examples, water and water-containing solvents such as mixtures of water and other solvent(s) are preferable. Of these, water is particularly preferable. The solvent does not necessarily have to be used in a proportion whereby the catechol is completely dissolved; an amount such that a small portion of the catechol is dissolved is sufficient to promote the reaction.

Further, the reaction is preferably carried out in the presence of acid such as an organic acid, inorganic acid or the like incorporated in the reaction system. Examples of organic acids include organic carboxylic acids such as acetic acid, propionic acid, trifluoroacetic acid, etc., and examples of inorganic acids include mineral acids such as sulfuric acid, hydrochloric acid, nitric acid, perchloric acid, phosphoric acid, etc. Organic acids can be used neat or in the form of aqueous solutions, and inorganic acids can be used in the form of aqueous solutions. Of these, an aqueous inorganic acid solution is preferable. In particular, a 50 to 80 wt % aqueous solution of sulfuric acid or a 50 to 80 wt % aqueous solution of perchloric acid is preferable. Organic acid or inorganic acid may be used in a proportion of from 1 to 100 moles, and preferably from 3 to 50 moles, per mole of catechol.

An organic acid per se, an aqueous organic acid solution, or an aqueous inorganic acid solution may also be used as a reaction solvent.

When necessary, the reaction may be carried out through the use of a catalyst. Examples of catalysts include Lewis acid catalysts such as $BF_3.O(C_2H_5)_2$; phase transfer catalysts such as sodium dodecyl sulfate, tetrabutylammonium halides, etc.; and so forth. The catalyst may usually be used in a proportion of from about 0.001 to 0.5 mole per mole of catechol.

The reaction is carried out by mixing catechol and peroxide, preferably with the addition of a reaction solvent and/or acid, and subjecting the mixture to any of such known processes as mechanical stirring, ultrasonic irradiation and the like. The solvent used is preferably a solvent which dissolves at least a small amount of the catechol or persulfate. The reaction can be carried out in the air at about standard atmospheric pressure. The reaction temperature is usually in the range of $-30°$ C. to the reflux temperature of the solvent, and is preferably approximately room temperature (for example, about 10 to about $30°$ C.). The reaction usually finishes in a period of about 1 to about 20 hours, although this depends on the amount of peroxide used, reaction solvent, reaction temperature, and the like.

Following the removal of impurities such as unreacted starting materials, by-products, solvents and the like from the reaction liquid by conventional processes such as extraction, distillation, washing, concentration, precipitation, filtration, drying, etc., post-treatment is performed by one or a combination of conventional processes such as adsorption, elution, distillation, precipitation, separation, chromatography, etc, so as to isolate HHTP.

For application on an industrial scale, the following method of HHTP separation is advantageously used: after the reaction, any precipitate is filtered off, by-products and the like are removed from the reaction liquid using adsorbent(s), and HHTP is separated using a predetermined solvent (such as water, acetone, or the like). One or more types of adsorbents are used selected from activated carbon, silica gel, activated alumina, activated kaolin, molecular sieves, and polymeric adsorbents.

In a batch operation, the amount of adsorbent(s) used for the treatment is not particularly limited; however, it is usually, for example, in a proportion of 1 to 50 parts by weight, preferably in a proportion of 2 to 25 parts by weight, and more preferably in a proportion of 5 to 20 parts by weight, per 100 parts by weight of HHTP produced.

When such treatment is continuously applied by filling a column with adsorbent(s), the amount of the adsorbent(s) used is not limited; the column may be formed with an amount of adsorbent(s) which does not impair the column's operation, and an elution process may be performed with a predetermined solvent. Such adsorbent(s) may be replaced or regenerated when the adsorption capability thereof has degraded.

HHTP may be produced as an anhydrate, or, depending on the post-treatment processes employed, produced in solvated form such as, e.g., a HHTP.hydrate (e.g., $HHTP.1H_2O$) or an acetone solvate of HHTP.

BEST MODE FOR CARRYING OUT THE INVENTION

The present invention will become more apparent through the following Examples, which are not intended to limit the scope of the disclosure.

The purity of HHTP obtained in each of Examples was measured by High Performance Liquid Chromatography (HPLC) under the following conditions:

Column: TOSOH TSK-GEL ODS-80TS (manufactured by Tosoh Corporation) 4.6×150 mm Mobile phase: methanol/water ($H_3PO_4$: 0.5 mol/l; $NaH_2PO_4$:0.5 mol/l)

Flow rate: 1.0 ml/min

EXAMPLE 1

34.2 g of ammonium persulfate (0.15 mol) was added to 16.5 g of catechol (0.15 mol) dispersed in 50 ml of a 70 wt % aqueous solution of sulfuric acid. The mixture was stirred for 7 hours at room temperature, and the resultant precipitate was then filtered and washed with water. 300 ml of acetone and 1.5 g of activated carbon were added to the precipitate, the mixture was stirred for 30 min at room temperature, and insoluble matter was subsequently filtered off from the mixture. 300 ml of ion-exchanged water was added to the filtrate, and then acetone was distilled off at distillation temperatures of 56 to $100°$ C. under normal pressure (101.3 kPa). The resultant precipitate was filtered and dried under reduced pressure to afford 14.2 g of crystals of HHTP (yield: 83.1%; purity>99%).

EXAMPLE 2

Reaction and post-treatment were carried out in a similar manner to that in Example 1, except for using 68.4 g of ammonium persulfate (0.30 mol) and 250 ml of a 60 wt % aqueous solution of perchloric acid, thereby yielding crystals of HHTP (yield: 72.6%; purity>99%).

EXAMPLE 3

Reaction and post-treatment were carried out in a similar manner to that in Example 1, except for using 68.4 g of ammonium persulfate (0.30 mol) together with 125 ml of a 60 wt % aqueous solution of perchloric acid and 125 ml of dichloroethane, thereby giving crystals of HHTP (purity>99%).

EXAMPLE 4

Reaction and post-treatment were carried out in a similar manner to that in Example 1, except that 8.5 g of 60 wt % hydrogen peroxide (0.15 mol) and 100 ml of 70 wt % sulfuric acid were used and reacted for 3 hours, thereby yielding crystals of HHTP (purity>99%).

EXAMPLE 5

Reaction and post-treatment were carried out in a similar manner to that in Example 1, except that 16.5 g of 31 wt % hydrogen peroxide (0.15 mol) and 100 ml of 70 wt % sulfuric acid were used and reacted for 3 hours, thereby affording crystals of HHTP (purity>99%).

EXAMPLE 6

Reaction and post-treatment were carried out in a similar manner to that in Example 1, except that 33 g of 31 wt % hydrogen peroxide (0.3 mol) and 100 ml of trifluoroacetic acid were used and reacted for 3 hours, thereby giving crystals of HHTP (purity>99%).

EFFECTS OF THE INVENTION

The present invention provides a method for allowing labile HHTP to be made highly pure in a simple and efficient manner. The method is very promising especially as a large-scale industrial production method.

Unlike the conventional method using transition metal compounds which are environmentally hazardous and liable to form complexes with HHTP, the method according to the invention uses peroxide, which does not form a complex with HHTP, for oxidative trimerization of catechol, so that HHTP possessing high purity can be manufactured in a simple manner.

The invention claimed is:

1. A method for producing 2,3,6,7,10,11-hexahydroxytriphenylene comprising reacting catechol with a peroxide.

2. A method according to claim 1, wherein the peroxide is a persulfate.

3. A method according to claim 1, wherein the peroxide is at least one member selected from the group consisting of sodium persulfate, potassium persulfate and ammonium persulfate.

4. A method according to claim 1, wherein the peroxide is ammonium persulfate.

5. A method according to claim 1, wherein the peroxide is hydrogen peroxide.

6. A method according to claim 1, wherein the peroxide is used in a proportion of from 0.5 to 10 moles per mole of catechol.

7. A method according to claim 2, wherein the persulfate is used in a proportion of from 0.5 to 10 moles per mole of catechol.

8. A method according to claim 1, wherein the reaction is carried out in the presence of acid.

9. A method according to claim 8, wherein the acid used is sulfuric acid or perchloric acid.

10. A method according to claim 8, wherein the acid used is a 50 to 80 wt % aqueous solution of sulfuric acid or a 50 to 80 wt % aqueous solution of perchloric acid.

* * * * *